United States Patent
Brown, Jr. et al.

[11] Patent Number: 5,126,446
[45] Date of Patent: Jun. 30, 1992

[54] PROCESS FOR 3-EXOMETHYLENECEPHAM SULFOXIDE ESTERS

[75] Inventors: Frank Brown, Jr.; Francis O. Ginah; Leonard L. Winneroski, Jr., all of Indianapolis, Ind.

[73] Assignee: Eli Lilly and Company, Indianapolis, Ind.

[21] Appl. No.: 638,467

[22] Filed: Jan. 4, 1991

[51] Int. Cl.$^5$ .............................. C07D 501/02
[52] U.S. Cl. ................... 540/230; 540/215; 540/222
[58] Field of Search .......... 540/222, 230, 215

[56] References Cited

U.S. PATENT DOCUMENTS

| | | | |
|---|---|---|---|
| 4,052,387 | 10/1977 | Kukolja | 544/22 |
| 4,075,203 | 2/1978 | Chou | 544/18 |
| 4,081,440 | 3/1978 | Kukolja | 260/239 |
| 4,165,315 | 8/1979 | Kukolja | 260/239 |
| 4,190,724 | 2/1980 | Chou | 544/16 |
| 4,289,695 | 9/1981 | Chou | 260/239 |
| 4,950,753 | 8/1990 | Copp et al. | 540/230 |

*Primary Examiner*—Nicholas S. Rizzo
*Attorney, Agent, or Firm*—James J. Sales; Leroy Whitaker

[57] ABSTRACT

3-Exomethylenecepham sulfoxide esters are obtained in improved yields via cyclization of 3-methyl-2-(4-chlorosulfinyl-2-oxo-3-amino-1-azetidinyl)-3-butenoic acid esters under anhydrous conditions with a Lewis acid-type Friedel-Crafts catalyst in the presence of a nitro compound, e.g., nitromethane, nitroethane, nitropropane or nitrobenzene.

39 Claims, 2 Drawing Sheets

PROCESS FOR 3-EXOMETHYLENECEPHAM SULFOXIDE ESTERS

BACKGROUND OF THE INVENTION

This invention relates to a process for the manufacture of intermediates for β-lactam antibiotics. In particular, it relates to an improved process for the manufacture of 7-substituted amino-3-exomethylenecepham ester sulfoxides.

The preparation of 3-exomethylenecepham sulfoxide esters is carried out by the known two-step process which comprises the conversion of a penicillin sulfoxide ester to a chlorosulfinylazetidinone followed by the cyclization of the latter to a 3-exomethylenecepham sulfoxide ester. The penicillin sulfoxide ester is converted to the intermediate chlorosulfinylazetidinone with an N-chloro halogenating agent as described by Kukolja in U.S. Pat. No. 4,165,315. The 4-chlorosulfinylazetidinone intermediates are described and claimed by Kukolja in U.S. Pat. No. 4,081,440. Chou, U.S. Pat. No. 4,075,203, describes the preparation of 3-exomethylenecepham sulfoxide ester via conversion of the penicillin sulfoxide ester in step 1 to the 4-chlorosulfinylazetidinone with an N-chloro halogenating agent in the presence of an alkylene oxide and calcium oxide. Later, Chou, U.S. Pat. No. 4,289,695, describes an improved process for 3-exomethylenecepham sulfoxide esters by employing an acid scavenging cross-linked polyvinylpyridine polymer in step 1.

Kukolja, U.S. Pat. No. 4,052,387, describes the cyclization of 4-chlorosulfinylazetidinones with a Lewis acid-type Friedel-Crafts catalyst, a Bronsted proton acid-type Friedel-Crafts catalyst or with a metathetic cation-forming agent. Subsequently, Chou, U.S. Pat. No. 4,190,724, describes and claims an improved process which comprises carrying out the Kukolja Friedel-Crafts catalyzed cyclization of a 4-chlorosulfinylazetidinone in the presence of oxo compounds such as ethers, ketones or phosphine oxides. Copp et al., U.S. Pat. No. 4,950,753, incorporated herein by reference, describes a further improvement of the Kukolja process which comprises carrying out the Friedel-Crafts cyclization in the presence of both an oxo compound of Chou and an unsaturated compound e.g., an alkene such as 1- or 2-hexene, a non-conjugated alkadiene such as 1,4-hexadiene, a cycloalkene such as cyclohexene, an allene, or a non-conjugated cycloalkadiene such as 1,4-cyclohexadiene. The present invention provides a further improvement of the Kukolja process which includes carrying out the Friedel-Crafts cyclization in the presence of a nitro compound, e.g., nitromethane, nitrobenzene, nitroethane, and nitrobenzene.

DESCRIPTION OF THE INVENTION

Figure 1:
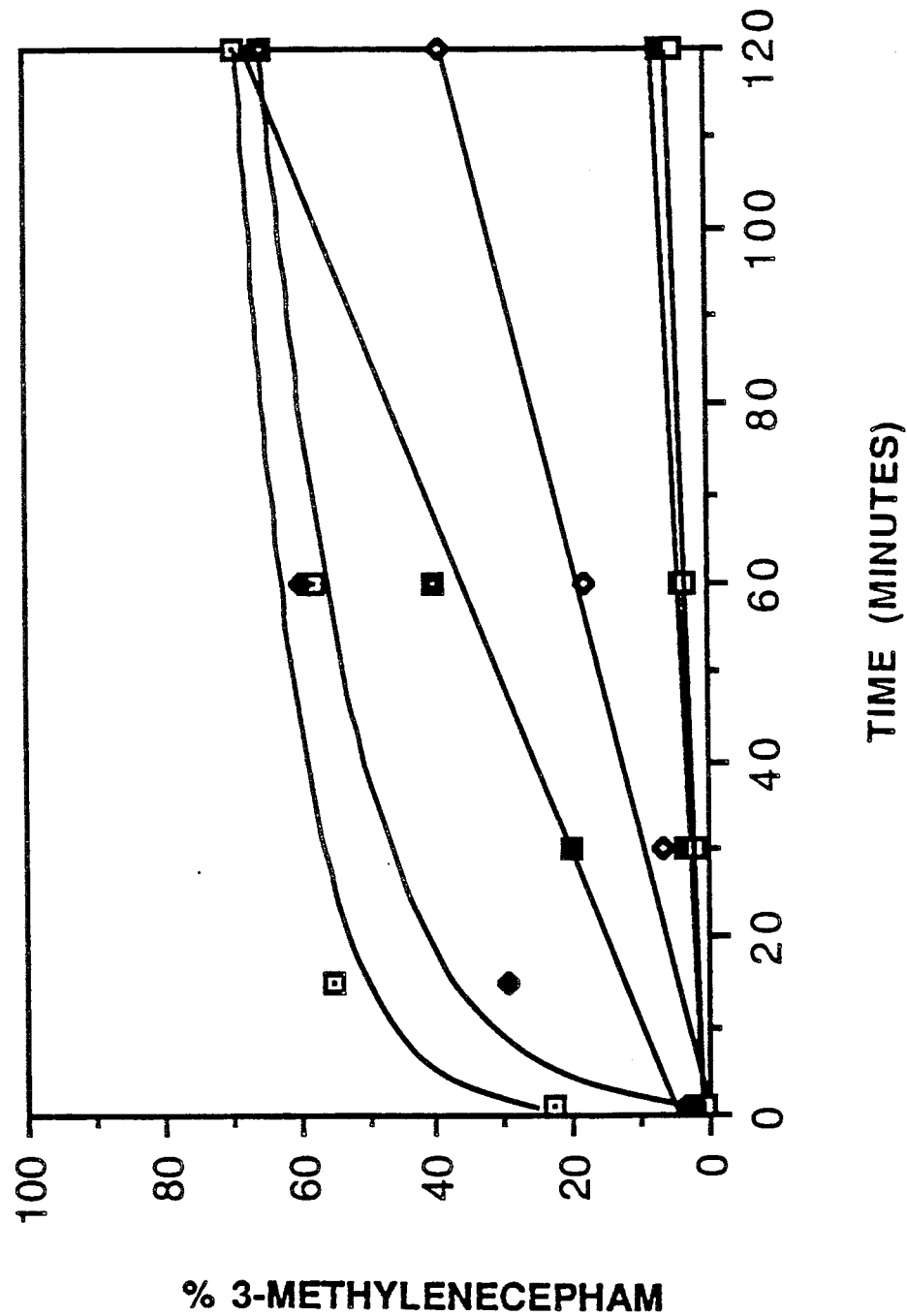
FIG. 1 is a graph illustrating reaction rates in cyclizing 4-chlorosulfinylazetidinones under various conditions.

According to the process of this invention, a chlorosulfinylazetidinone is reacted in an inert solvent with a Lewis acid-type Friedel-Crafts catalyst of the type which forms a complex with the chlorosulfinylazetidinone, in the presence of a nitro compound. In a preferred embodiment, the Friedel-Crafts catalyst is stannic chloride, the nitro compound is nitromethane, and the reaction takes place in the presence of an oxo compound, e.g., an ether, ketone or phosphine oxide, and an alkene, cycloalkene, allene or cyclodiene. The 3-exomethylenecepham sulfoxide ester product is obtained in improved yields, generally in the range of between about 2% and about 4% of isolated product, and at improved reaction rates.

The process of this invention provides a 3-exomethylenecepham sulfoxide ester represented by the formula 1:

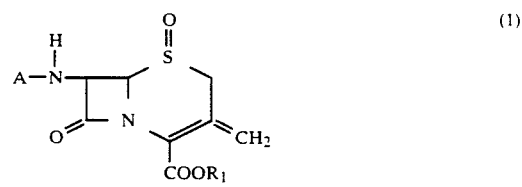

(1)

wherein A is an amino protecting group or a group of the formula

wherein R is the residue of a carboxylic acid RCOOH and $R_1$ is a carboxy-protecting group, by cyclizing a chlorosulfinylazetidinone represented by the formula (2)

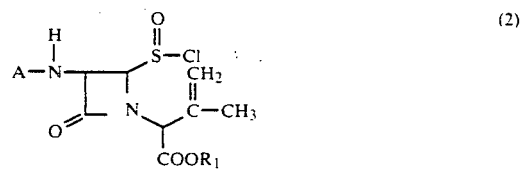

(2)

with a Lewis acid-type Friedel-Crafts catalyst and nitro compound under substantially anhydrous conditions for a time and at a temperature sufficient to result in the compound of formula (1).

The term "residue of a carboxylic acid" includes those 7-position side chains known in the cephalosporin and carbocephalosporin arts, and those 6-position side chains known in the penicillin art. Normally, these side chains are residues of $C_1$–$C_{20}$ carboxylic acids, and are exemplified when R is hydrogen; $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl, or trifluoromethylthio; naphthyl, a phenyl or substituted phenyl group of the formula

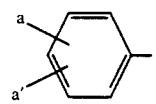

wherein a and a' independently are hydrogen, halogen, hydroxy, $C_1$–$C_4$ alkoxy, $C_1$$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, carboxymethyl, $C_1$–$C_4$ haloalkyl or $C_1$–$C_4$ perhaloalkyl; a group of the formula

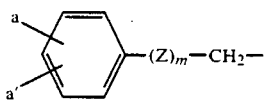

wherein a and a' have the same meanings as defined above, Z is O or S, and m is 0 or 1; an arylmethyl group of the formula $R_3$—$CH_2$— wherein $R_3$ is naphthyl, thienyl, furyl, benzothienyl, benzoaminothiazyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and such aryl groups substituted by amino, hydroxy, halogen, $C_1$-$C_4$ alkyl, $C_1$-$C_4$ alkoxy, phenyl, substituted phenyl, or $C_1$-$C_4$ alkylsulfonylamino; a substituted methyl group of the formula

wherein $R_4$ is cyclohex-1,4-dienyl, a phenyl or substituted phenyl of the formula

wherein a and a' are as defined above, or $R_4$ is $R_3$ as defined above, and Q is hydroxy, $C_1$-$C_4$ alkanoyloxy, carboxy, sulfo, amino, sulfoamino, or a substituted amino group of the formula

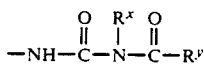

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$-$C_3$ alkylsulfonyl, $C_1$-$C_3$ alkyl, or $C_1$-$C_4$ alkanoyl; or Q is a substituted amino group of the formula

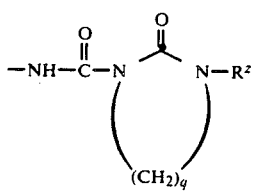

wherein $R^z$ has the same meaning as defined above, and q is 2 or 3; or Q is a substituted amino group of the formula

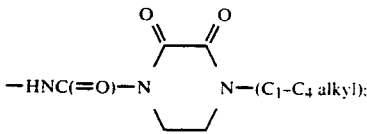

or Q is a benzamido group of the formula

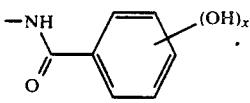

wherein X is 1 to 3; or Q is a pyridone or hydroxy-substituted pyridonylcarbonylamino group of the formula

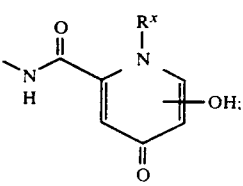

wherein $R^x$ is as defined above; or Q is a pyridylcarbonylamino group of the formula

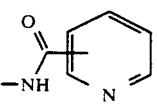

such group optionally substituted by $C_1$-$C_4$ alkyl, amino, carboxy, hydroxy or halogen; or Q is an imidazolyl or pyrazolyl group of the formula

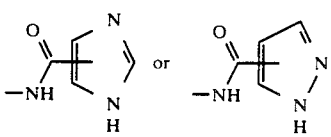

and such imidazolyl or pyrazolyl optionally substituted by $C_1$-$C_4$ alkyl, carboxy, amino, or halogen; or Q is a benzpyridazin-4-one group or tautomer thereof represented by the formula

or

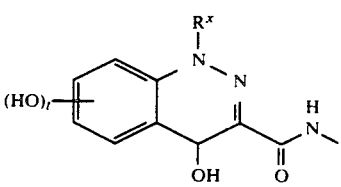

wherein $R^x$ is as defined above, and t is 1 to 3; or Q is a benzpyranone group of the formula

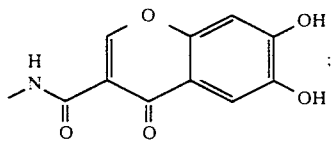

or R is a group of the formula

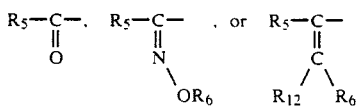

wherein $R_5$ is $R_3$ or $R_4$ as defined above, $R_{12}$ is hydrogen or halogen, and $R_6$ is hydrogen, $C_1$–$C_4$ alkyl, $C_1$–$C_4$ alkyl substituted by halogen, a carboxy-substituted alkyl or cycloalkyl group represented by the formula

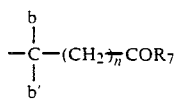

wherein b and b' independently are hydrogen or $C_1$–$C_3$ alkyl, n is 0, 1, 2, or 3; and b and b' when taken together with the carbon to which they are bonded form a 3- to 6-membered carbocyclic ring, and $R_7$ is hydroxy, $C_1$–$C_4$ amino, $C_1$–$C_4$ alkylamino, or di($C_1$–$C_4$ alkyl)amino; or $R_6$ is $C_1$–$C_4$ substituted by phenyl or phenyl substituted by one or two of the same or different groups selected from among $C_1$–$C_4$ alkyl, hydroxy, halogen, carboxy or protected carboxy; or $R_6$ is $C_1$–$C_4$ alkyl substituted by amino or protected amino; or $R_6$ is $C_1$–$C_4$ alkenyl; or $R_6$ is a cyclic lactam group of the formula

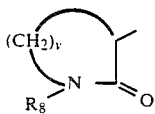

wherein v is 2–4 and $R_8$ is hydrogen or $C_1$–$C_3$ alkyl; or $R_6$ is an aryl methyl group of the formula

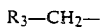

wherein $R_3$ has the same meanings as defined hereinabove.

The term "carboxy-protecting group" as used in the specification refers to one of the ester derivatives of a carboxylic acid group commonly employed to block or protect the carboxylic acid group while reactions are carried out on other functional groups on the compound. Examples of such carboxylic acid protecting groups include 4-nitrobenzyl, 4-methylbenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the ring system and can be removed at the appropriate point without disrupting the remainder of the molecule. A preferred carboxylic acid protecting group is the allyl group. Similar carboxy-protecting groups used in the cephalosporin, penicillin and peptide arts can also be used to protect carboxy group substituents of the azetidinone. Further examples of these groups are found in E. Haslam, "Protective Groups in Organic Chemistry", J.G.W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The related term "protected carboxy" denotes that a carboxy group is substituted with one of the above carboxy-protecting groups.

The term "amino-protecting group" refers to substituents of the amino group commonly employed to block or protect the amino functionality while reacting other functional groups on the compound. Examples of such amino-protecting groups include the formyl group, the trityl group, the phthalimido group, the groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" denotes that an amino is substituted with an amino-protecting group discussed above.

In the above definition of the compounds represented by the formula (1), $C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$–$C_6$ alkyl substituted by cyano refers to cyanomethyl, cyanomethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$–$C_6$ alkyl substituted by $C_1$–$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$-$C_6$ alkyl substituted groups.

When in the formula (1) A is a group of the formula

and R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

When R is a substituted phenyl group and a' or a is a $C_1$-$C_4$ haloalkyl or $C_1$-$C_4$ perhaloalkyl, examples of such substituents include chloromethyl, iodomethyl, trichloromethyl, trichloroethyl, 2-bromo-2-methylpropyl, chloropropyl, and fluoromethyl.

Examples wherein R is a group represented by the formula

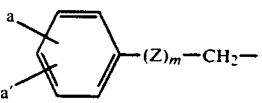

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples when R is $R_3CH_2$— wherein $R_3$ is an aryl group are: naphthyl, 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl and benzoaminothiazoyl, and like aryl groups optionally substituted by amino, $C_1$-$C_4$ alkylsulfonylamino, hydroxy, halo, $C_1$-$C_4$ alkyl or $C_1$-$C_4$-alkoxy groups.

Examples wherein R is a substituted methyl group represented by the formula $R_4$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

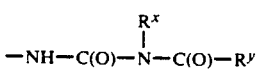

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethyl-carbamoylureido)-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

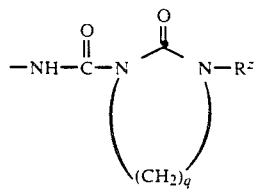

examples are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methyl-sulfonylimidazolidin-2-one-1-yl)-2-(2-thienyl)acetyl, and 2-[(3-acetylhexahydropyrimidin-2-one-1-yl)carbonyl-amino]-2-phenylacetyl; and when Q is a hydroxy-substituted benzamido group represented by the formula

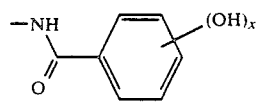

examples of such acyl groups are 2-(2,4-dihydroxy-benzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin-4-one-6-yl-carbonylamino. When Q is a pyridylcarbonylamino group examples are e.g., pyridin-3-ylcarbonylamino, 4-amino-pyridin-3-ylcarbonylamino, 5-chloropyridin-2-ylcarbonyl-amino, 3-carboxypyridin-4-ylcarbonylamino, and 4-amino-pyridino-2-ylcarbonylamino. When Q is an imidazole or pyrazole group as defined above examples include e.g., 2-aminoimidazol-4-ylcarbonylamino, 5-carboxy-2-methyl-imidazol-4-ylcarbonylamino, 5-carboxypyrazol-3-ylcarbon-ylamino, 3-aminopyrazol-4-ylcarbonylamino and 4-hydroxy-pyrazol-5-ylcarbonylamino. When Q is a benzpyridazin-4-one-3-ylcarbonylamino group, examples of Q are represented by the formulae

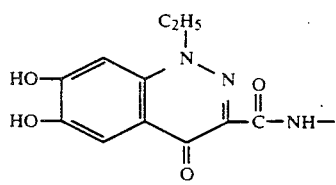

and

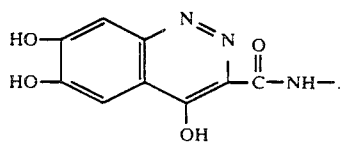

Examples when R is a keto group or an oximino-substituted group represented by the formulae

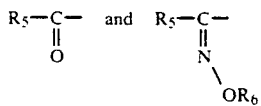

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyimino-acetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-amino-thiazol-4-yl)-2-(2-carboxyprop-2-yl)oxyiminoacetyl, 2-(2-aminothiazol-4-yl)-2-(2-carbamoylprop-2-yl)oxyimino-acetyl, 2-(5-amino-1,3,4-thiadiazol-2-yl)-2-methoxyimino-acetyl, 2-(2-amino-thiazol-4-yl)-2-(pyrrolidin-2-one-yl)-oxyiminoacetyl, 2-(2-aminothiazol-4-yl)-2-(1-methyl-pyrrolidin-2-one-3-yl)oxyiminoacetyl, 2-phenyl-2-(pyrro-lidin-2-one-3-yl)oxyiminoacetyl, 2-(2-aminooxazol-4-yl)-2-(1-ethyl-pyrrolidin-2-one-3-yl)oxyiminoacetyl, 2-(2-amino-thiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

Examples when R is a group of the formula

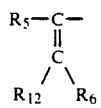

may be found in Hamashima, U.S. Pat. No. 4,634,617, incorporated herein by reference. Exemplary substituents are for $R_{12}$, hydrogen, for $R_5$, phenyl, furyl, thienyl, oxazolyl, isoxazolyl, optionally protected aminoisoxazolyl, thiazolyl, optionally protected aminothiazolyl, thiadiazolyl, and aminothiazolyl, and for $R_6$, $C_1-C_3$ alkenyl, especially methylene.

When $R_6$ is $C_1-C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenylpropyl, 4-hydroxy-2-phenylpropyl, 3-phenylbutyl and like phenylalkyl groups.

When $R_6$ represents $C_1C_4$ alkyl substituted by amino or protected amino, examples include 2-aminoethyl, 3-aminopropyl, 4-aminobutyl, 2-aminopropyl and such groups wherein the amino group is protected by an amino-protecting group.

When $R_6$ is a $C_2-C_4$ alkenyl group, examples include allyl, butene-2, butene-3, butene-1, and like groups.

The Lewis acid-type catalysts are characterized by the presence of a vacant orbital which can accept an available electron pair, either unshared, e.g. on an oxygen, sulfur, or halide atom, or in a $\pi$ orbital, of a Lewis base type compound to form a covalent bond. Exemplary of suitable Lewis acid-type metal catalysts are aluminum chloride, stannic chloride, stannic bromide, zinc chloride, zinc bromide, antimony pentachloride, titanium tetrachloride, ferric chloride, gallium trichloride, zirconium tetrachloride, mercuric chloride, chromium trichloride and like metal halide agents exhibiting Friedel-Crafts type catalytic activity. Preferred of such catalysts are stannic chloride, zirconium tetrachloride and titanium tetrachloride. Stannic chloride is especially preferred. The catalyst employed is preferably in the amount of between about 1.0 and 3 moles per mole of sulfinyl chloride (2).

The nitro compounds include $C_1-C_6$ nitroalkanes and nitro substituted aryls, and are represented by nitromethane, nitroethane, 1-nitropropane, 2-nitropropane, p-nitrotoluene, alpha-nitrotoluene, and nitrobenzene. Nitromethane, 1-nitropropane, nitroethane, and nitrobenzene are preferred. Nitromethane is especially preferred. The nitro compound employed is preferably in the amount of between about 1 and about 4 moles per mole of the sulfinyl chloride (2).

4-Chlorosulfinylazetidinones of formula (2) used in the process are known compounds and are described by Kukolja in U.S. Pat. No. 4,081,440, incorporated herein by reference. Examples of the starting materials which are used in the process are t-butyl 3-methyl-2-(4-chlorosulfinyl-2-oxo-3-phenylacetylamino-1-azetidinyl)-3-butenoate, t-butyl 3-methyl-2-(4-chlorosulfinyl-2-oxo-3-phenoxyacetylamino-1-azetidinyl)-3-butenoate, diphenylmethyl 3-methyl-2-(4-chlorosulfinyl-2-oxo-3-phenoxyacetylamino-1-azetidinyl)-3-butenoate, p-methoxybenzyl 3-methyl-2-(4-chlorosulfinyl-2-oxo-3-phenylacetylamino-1-azetidinyl)-3-butenoate, p-nitro-benzyl 3-methyl-2-(4-chlorosulfinyl-2-oxo-3-phenoxy-acetylamino-1-azetidinyl)-3-butenoate, diphenylmethyl 3-methyl-2-(4-chlorosulfinyl-2-oxo-3-benzoylamino-1-azeti-dinyl)-3-butenoate, p-nitrobenzyl 3-methyl-2-[4-chloro-sulfinyl-2-oxo-3-(α-t-butyloxycarbonylaminophenylacetyl-amino)-1-azetidinyl-3-butenoate, benzyl 3-methyl-2-(4-chlorosulfinyl-2-oxo-3-phenoxyacetylamino-1-azetidinyl)-3-butenoate, and benzhydryl 3-methyl-2-(4-chlorosulfinyl-2-oxo-3-acetylamino-1-azetidinyl)-3-butenoate. Preferred azetidinones are represented by formula (2) where A is a group of the formula

and R is benzyl, phenoxymethyl or thienylmethyl. A preferred ester group $R_1$ of formula 2 is benzyl or substituted benzyl, especially p-nitrobenzyl.

The process is carried out at a temperature between about $-15°$ C. and about 60° C. and preferably between about $-10°$ to about 0° C., and in an inert organic solvent. Solvents which may be used are described by Kukolja in U.S. Pat. No. 4,052,387, which is incorporated herein by reference and wherein the basic cyclization process is described. Preferred solvents are aprotic and include the aromatic hydrocarbons such as benzene, toluene, xylene, chlorobenzene and the like, and the halogenated hydrocarbons such as chloroform, methylene chloride, carbon tetrachloride, 1,2-dichloroethane, 1,1,2-trichloroethane, and the like. Especially preferred solvents are benzene and toluene.

As noted above, the process is carried out under substantially anhydrous conditions. Trace amounts of water are tolerable; however, it is desirable to maintain the reaction mixture in the process as dry as possible.

In a preferred embodiment of the invention, an oxo compound is also present during the cyclization. The oxo compounds used in the process are described by Chou, U.S. Pat. No. 4,190,724, which is incorporated herein by reference, and are selected from among the group $R_2-O-R_2,Z$

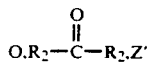

$C=O$ and $(R'_2)_3P\rightarrow$, wherein each $R_2$ is independently $C_1-C_4$ alkyl; each $R'_2$ is independently $C_1-C_4$ alkyl, $C_5-C_6$ cycloalkyl, phenyl or phenyl substituted by $C_1-C_4$ alkyl, $C_1-C_4$ alkoxy, or halogen; Z is $(CH_2)_m$, $-CH_2-CH_2-O-CH_2-CH_2-$, or $-CH_2-O-CH_2CH_2CH_2-$; m is 4 or 5; and Z' is

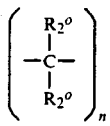

wherein each of $R°_2$ is hydrogen or $C_1-C_4$ alkyl, and n is 3 to 6. Preferred oxo compounds are diethyl ether, di-n-propyl ether, acetone and methylethyl ketone. Especially preferred is diethylether. The oxo compound employed in the process is preferably in an amount corresponding to between about 0.75 and about 2 moles per mole of the sulfinyl chloride (2).

In another preferred embodiment of the invention, an unsaturated compound is present during the cyclization. The unsaturated compound which can be used in the process may be selected from among $C_2-C_{10}$ olefins, $C_5-C_{10}$ cycloolefins, non-conjugated $C_5-C_{10}$ diolefins, $C_3-C_{10}$ allenes, and non-conjugated $C_6-C_{10}$ cyclodiolefins. Examples of such alkenes, alkadienes, cycloalkenes, allenes and cyclodienes include, for example, the alkenes ethylene, propylene, 1-butene, 2-butene, 1-pentene, 2-pentene, 1-hexene, 3-hexene, 1-heptene, 3-heptene, 1-octene, 2-nonene, 3-nonene, 1-decene, 5-decene, and like terminal and non-terminal alkenes; non-conjugated alkadienes such as 1,4-pentadiene, 1,4-hexadiene, 3-methyl-1,4-hexadiene, 1,5-hexadiene, 1,5-heptadiene, 1,6-heptadiene, and like dienes; non-conjugated cyclodienes such as 1,4-cyclohexadiene, 1,4-cycloheptadiene, and the like; allenes such as allene, methylallene (1,2-butadiene), dimethylallene (2,3-pentadiene), and the like; cycloalkenes such as cyclopentene, 1-methylcyclopent-2-ene, cyclohexene, cycloheptene, cyclooctene, and the like. The alkene, alkadiene or allene may be straight chained or branched and may be substituted with an inert group, preferably on a saturated carbon atom of the alkene. For example, the unsaturated compound may be substituted with alkyl such as methyl, ethyl or isopropyl; halogen (preferably in a non-allylic position); an esterified carboxy group; an aromatic group such as phenyl or tolyl; nitro; cyano; and alkoxy such as methoxy or ethoxy; and like aprotic substituents which are inert under the conditions of the process.

Non-terminal alkenes may be used in either the cis or trans forms. Preferred unsaturated compounds of the invention are the alkenes, e.g., 1-pentene, 2-pentene, 1-hexene, 2-hexene, 1-heptene, 1-octene and 1-decene; and the cycloalkenes, cyclopentene and cyclohexene. Especially preferred is 1-hexene.

The unsaturated compound employed in the process is preferably present in an amount corresponding to between about one mole to about two moles per mole of sulfinyl chloride (2). An especially preferred amount is between about one mole and about 1.5 mole of unsaturated compound per mole of sulfinyl chloride (2). Best results are achieved with 1 mole of unsaturated compound, especially 1-hexene, per mole of the compound of formula (2).

In an especially preferred embodiment of the invention, the compound of formula (1) is formed by reacting the 4-chlorosulfinylazetidin-2-one of formula (2) with between about 1.5 and about 3 moles of stannic chloride per mole of the azetidinone, between about 0.75 and about 2 moles of ethyl ether per mole of the azetidinone, between about 1 and 2 moles of 1-hexene per mole of the azetidinone, and about 1 to 4 moles of nitromethane per mole of the azetidinone, in an inert solvent under substantially anhydrous conditions at a temperature between about −10° C. and about 0° C. The best yields have been obtained by using 2.5 molar equivalents of nitromethane and 1.0 molar equivalents of 1-hexene with ethylether and stannic chloride.

The process of this invention is carried out generally as follows. The 4-chlorosulfinylazetidinone (2) is dissolved in an anhydrous inert organic solvent. The solution is cooled to a temperature of about 0° C. to about 15° C. The nitro compound is added to the solution, cooled to about −10° C., and stirred. The catalyst, and, if desired, the oxo compound and unsaturated compound, in a solvent, are cooled to about −10° C. and added to the sulfinyl chloride solution. The solution is stirred under nitrogen and allowed to reach about room temperature. The complex is separated from the reaction mixture, e.g., by filtration or centrifugation, is washed with an inert solvent and decomposed with a lower alcohol such as methyl alcohol. The 3-exomethylenecepham sulfoxide ester forms as a solid precipitate, is filtered, washed and dried for subsequent use.

As was mentioned hereinabove, the use of the above-defined nitro compounds in the known cyclization process results in improved reaction rates and yields of 3-exomethylenecepham sulfoxide ester. Yields of sulfoxide ester generally obtained are between 2% to 4% greater than control preparations. Such increased yields and improved reaction rates are of substantial economic value in the manufacture of large quantities of the 3-exomethylenecepham sulfoxide ester. The 3-exomethylenecepham sulfoxide ester (1) is used as an intermediate in the preparation of cephalosporin antibiotics, for example, cefaclor, 7β-phenylglycylamino-3-chloro-3-cephem-4-carboxylic acid by known methods. The intermediate (1) also may be used to prepare cephalexin, 7β -phenylglycylamino-3-methyl-3-cephem-4-carboxylic acid. Accordingly, the increased yields realized in the process of this invention result in increased production of these valuable antibiotic compounds.

The manner in which the nitro compounds function to provide increased yields of (1) at improved reaction rates has as yet not been determined. The possibility exists that the nitro compounds function to allow greater degrees of freedom for the insoluble metal sulfinyl chloride complex to participate in the ring closure reactions as opposed to the formation of byproducts. However, whether the nitro compound function to select the desired reaction to the detriment of those competing reactions as described or in some other manner is uncertain at present.

The following Experimental Section provides further description of the invention but is not to be construed as limitations thereof.

EXPERIMENTAL SECTION

General

The nitro compounds (nitromethane, nitroethane, 1-nitropropane and nitrobenzene), were dried with alumina B (activity 1). Toluene was dried using a type 4A molecular sieve. All reactions were run under dry nitrogen environments. The assay for the 3-methylenecephem products (formula 1) was performed using an HPLC (a 4.5 mm×5.0 cm, octyl encapped, 3 micron column, 254 nm wave length setting, 1.7 ml/min flow rate, and a 32% tetrahydrofuran, 0.5% phosphoric acid in water mobile phase was used). $^1$H NMR spectra were taken in CDCl$_3$ and recorded on a QE-300 (300 MHz) spectrometer. Abbreviations are as follows: s-singlet; d-doublet; t-triplet; q-quartet, m-multiplet.

Preparation 1

3-Methyl-2-(2-chlorosulfinyl-4-oxo-3-imido-1-azetidinyl)-3-butenoate (referred to herein as sulfinyl chloride).

For preparation of the titled product, the following was carried out. A one liter, three-necked round bottomed flask was equipped with a mechanical stirrer, Dean-Stark trap, condensor fitted with a nitrogen inlet, and a thermometer. The reaction flask was then charged with 29.48 g of wet poly (4-vinyl pyridine/divinylbenzene copolymer) (KF=44.9% water) and 796 mL of toluene. This slurry was heated to reflux (110° to 112° C.) under a nitrogen atmosphere until 160 mL of toluene azeotrope was collected via the Dean-Stark apparatus. The slurry was cooled to 60° C. with an ice bath before 49.28 g (97.8% purity, 96.1 mmoles) of (1B)-6-[(phenoxyacetyl)amino]penicillanic acid, (4-nitrophenyl)methyl ester-1-oxide and 21.86 g (12.1 mmoles, 1.26 equivalents) of N-chlorophthalimide were added to the reaction flask. Toluene (20 mL) was used to rinse the reagents into the flask. The mixture was heated to reflux for 120 minutes (timing was started at 109° C.) and an additional 59 mL of toluene azeotrope was collected. The reaction mixture was then immediately cooled to 15° C. and filtered and the solid polymer/phthalimide cake was washed with 104 mL of toluene and discarded. The yellow sulfinyl chloride solution was either used immediately or stored in 0° to 5° C. under argon pending its use.

$^1$H NMR: (CDCl$_3$, 300 MHz, ppm) 1.92 (s, 3H, CH$_3$), 4.50:4.56 (AB, 2H, J=15.1 Hz, side chain CH$_2$), 4.99 (s, 1H, olefinic CH$_2$), 5.06 (s, 1H, —CHCOOpNB), 5.22 (d, 1H, J=1.6 Hz, olefinic CH$_2$), 5.25:5.33 (AB, 2H, J=12.9 Hz, pNB CH$_2$), 5.53 (d, 1H, J=4.6 Hz, azetidinone H), 6.27 (dd, 1H, J=4.6 Hz and 10.8 Hz, azetidinone H), 6.90 (dd, 2H, J=7.4 Hz and 8.5 Hz, side chain ArH), 7.01 (t, 1H, J=7.4, side chain ArH), 7.30 (dd, 2H, J=7.4 Hz and 8.5 Hz, side chain ArH), 7.50 (AA'BB', 2H, J=8.9 Hz, pNB ArH), 7.98 (d, 1H, J=10.8 Hz, N-H), 8.23 (AA'BB', 2H, J=8.9 Hz, pNB ArH).

EXAMPLES

In the following examples, 3-methylene-7-[(phenoxyacetyl)-amino]cepham-4-carboxylic acid, (4-nitrophenyl)methyl ester, 1-oxide (1) was produced. Table 1 summarizes the results of the Examples.

EXAMPLE 1

A 500 mL three-necked round bottomed flask was equipped with a mechanical stirrer, a nitrogen inlet, and a thermometer. The reaction flask was charged with 220 mL of a toluene solution of sulfinyl chloride (25.5 mmoles based on (1B)-6-[(phenoxyacetyl)amino]-penicillanic acid, (4-nitrophenyl)methyl ester-1-oxide. In a separate 50 mL flask was added 10 mL of toluene and diethyl ether [2.5 mL (1.76 g) 23.9 mmoles, and the solution was cooled to 0° to −5° C. Tin (IV) chloride [5.1 mL (11.36 g) 43.6 mmoles] was added to the toluene/ diethyl ether solution and the resultant slurry was immediately cooled to 0° C. with an acetone/dry ice bath. The toluene solution of sulfinyl chloride was cooled to 15° C. and the tin (IV) chloride/diethyl ether/toluene slurry was added to the sulfinyl chloride in 5 to 10 seconds using 5 mL of toluene rinse. The resultant slurry was allowed to exotherm to 21° to 23° C. and stir for 18 hours under nitrogen.

The slurry was filtered, washed with 25 mL of toluene and returned to the reaction flask with 70 mL of methyl alcohol. The resultant slurry was stirred and allowed to crystallize at 21° to 23° C. for 15 minutes. The slurry was then cooled to 0° to 5° C. and stirred for another three hours and forty-five minutes. At two hours into this methyl alcohol treatment, 15 mL of deionized water was added.

The slurry was filtered and the product was washed with 30 mL of methyl alcohol. The light colored solid was dried in a vacuum oven at 45° to 60° C. for 15 to 16 hours. The assay corrected isolated yield of 3-methylene-7-[(phenoxyacetyl)-amino] cepham-4-carboxylic acid, (4-nitrophenyl)methyl ester, 1-oxide (1) was 68.1% (9.21 g, theoretical = 12.74 g) and the purity was determined to be 94.2% by replicate HPLC assay.

$^1$H NMR: (CDCl$_3$, 300 MHz, ppm) 3.57:3.74 (AB, 2H, J = 14.1 Hz, CH$_2$), 4.55 (s, 2H, side chain CH$_2$), 4.89 (d, 1H, J = 4.80 Hz, azetidinone H), 5.28 (s, 2H, pNB CH$_2$), 5.31 (s, 1H, —CHCOOpNB), 5.48 (d, 1H, J = 1.50 Hz, exo CH$_2$), 5.78 (s, 1H, exo CH$_2$), 6.03 (dd, 1H, J = 4.80 Hz and 10.70 Hz, azetidinone H), 6.93 (dd, 2H, J = 8.30 Hz and 7.40 Hz, side chain ArH), 7.0 (t, 1H, J = Hz, side chain ArH), 7.29 (dd, 2H, J = 8.30 Hz and 7.40 Hz, side chain ArH), 7.49 (AA'BB', 2H, J = 8.90 Hz, pNB ArH), 8.11 (d, 1H, J = 10.70 Hz, N-H), 8.25 (AA'BB',2H, J = 8.90 Hz, pNB ArH).

EXAMPLE 2

Example 1 (above) was repeated except: the toluene solution of sulfinyl chloride was cooled to −50° C. before the 0° C. tin (IV) chloride/diethyl ether/toluene slurry was added. No water was added during the methyl alcohol stir. The assay corrected isolated yield of (1) was 65.3% (8.5 g, theoretical = 12.33 g) and the purity was determined to be 94.7% by replicate HPLC assay.

EXAMPLE 3

Example 1 (above) was repeated except: the toluene solution of sulfinyl chloride was cooled to −10° C. before the 0° C. tin (IV) chloride/diethyl ether/toluene slurry was added. No water was added during the methyl alcohol stir. The assay corrected isolated yield of (1) was 66.3% (8.45 g, theoretical = 12.33 g) and the purity was determined to be 96.7% by replicate HPLC assay.

EXAMPLE 4

Example 1 (above) was repeated except: no diethyl ether was utilized in the reaction. No water was added during the methyl alcohol stir. The assay corrected isolated yield of (1) was 50.5% (10.15 g, theoretical = 19.58 g) and the purity was determined to be 97.3% by replicate HPLC assay.

EXAMPLE 5

A 500 mL three-necked round bottomed flask was equipped with a mechanical stirrer, a nitrogen inlet, and a thermometer. The reaction flask was charged with 192 mL of a toluene solution of sulfinyl chloride (25.5 mmoles based on (1B)-6-[(phenoxyacetyl)amino]-penicillanic acid, (4-nitrophenyl)methyl ester-1-oxide. In a separate 50 mL flask was added 10 mL of toluene. This toluene was cooled to 0° to −5° C. before tin (IV) chloride [5.1 mL (11.36 g) 43.6 mmoles] was added. The resultant solution was immediately cooled to −10° C. with an acetone/ dry ice bath. Nitromethane [3.5 mL (3.94 g) 64.6 mmoles] was added to the sulfinyl chloride solution and the resultant solution was cooled to −10° C. with an acetone/dry ice bath. The tin (IV) chloride/toluene solution was added to the −10° C. sulfinyl chloride solution in 5 to 10 seconds using 5 mL of toluene rinse. The resultant slurry was allowed to exotherm to 21° to 23° C. and stir for four hours under nitrogen.

The slurry was filtered, washed with 25 mL of toluene and returned to the reaction flask with 70 mL of methyl alcohol. The resultant slurry was stirred and allowed to crystallize at 21° to 23° C. for 15 minutes. The slurry was then cooled to 0° to 5° C. and stirred for another three hours and forty-five minutes. At two hours into this methyl alcohol treatment, 15 mL of deionized water was added.

The slurry was filtered and the product was washed with 30 mL of methyl alcohol. The light colored solid was dried in a vacuum oven at 45° to 60° C. for 15 to 16 hours. The assay corrected isolated yield of (1) was 60.9% (7.96 g, theoretical = 12.74 g) and the purity was determined to be 97.4% by replicate HPLC assay.

EXAMPLE 6

Example 5 (above) was repeated except: 1-hexene [3.2 mL (2.17 g) 25.8 mmoles] was also added to the toluene solution of sulfinyl chloride prior to the tin (IV) chloride/toluene addition The assay corrected isolated yield of (1) was 65.2% (8.47 g, theoretical = 12.74 g) and the purity was determined to be 98.0% by replicate HPLC assay.

EXAMPLE 7

A 500 mL three-necked round bottomed flask was equipped with a mechanical stirrer, a nitrogen inlet, and a thermometer. The reaction flask was charged with 179 mL of a toluene solution of sulfinyl chloride (24.7 mmoles based on (1B)-6-[(phenoxyacetyl)amino]-penicillanic acid, (4-nitrophenyl) methyl ester-1-oxide). In a separate 50 mL flask was added 10 mL of toluene and diethyl ether [2.4 mL (1.70 g) 22.9 mmoles], and the solution was cooled to 0° to −5° C. Tin (IV) chloride [4.9 mL (10.91 g) 41.9 mmoles] was added to the toluene/diethyl ether solution and the resultant slurry was immediately cooled to and held at 0° C. with an acetone/dry ice bath. 1-Hexene [3.1 mL (2.10 g) 25.0 mmoles] was added to the sulfinyl chloride solution and the resultant solution was cooled to 10° C. The 0° C. tin (IV) chloride/diethyl ether/toluene slurry was added to the sulfinyl chloride in 5 to 10 seconds using 5 mL of toluene rinse. The resultant slurry was allowed to exotherm to 21° to 23° C. and stir for four hours under nitrogen.

The slurry was filtered, washed with 25 mL of toluene and returned to the reaction flask with 80 mL of methyl alcohol. The resultant slurry was stirred and allowed to crystallize at 21° to 23° C. for 15 minutes. The slurry was then cooled to 0° to 5° C. and stirred for another three hours and forty-five minutes. No water was added during the methyl alcohol stir.

The slurry was filtered and the product was washed with 30 mL of methyl alcohol. The light colored solid was dried in a vacuum oven at 45° to 60° C. for 15 to 16 hours. The assay corrected isolated yield of (1) was 70.0% (8.9 g, theoretical=12.34 g) and the purity was determined to be 97.1% by replicate HPLC assay.

EXAMPLE 8

Example 5 (above) was repeated except: diethyl ether [2.5 mL (1.76 g) 23.9 mmoles] was utilized as described in Example 1. The assay corrected isolated yield of (1) was 71.1% (9.60 g, theoretical=12.74 g) and the purity was determined to be 94.3% by replicate HPLC assay.

EXAMPLE 9

A 500 mL three-necked round bottomed flask was equipped with a mechanical stirrer, a nitrogen inlet, and a thermometer. The reaction flask was charged with 179 mL of a toluene solution of sulfinyl chloride (24.7 mmoles based on (1B)-6-[(phenoxyacetyl)amino]-penicillanic acid, (4-nitrophenyl) methyl ester-1-oxide. In a separate 50 mL flask was added 10 mL of toluene and diethyl ether [2.4 mL (1.70 g) 22.9 mmoles], and the solution was cooled to 0° to −5° C. Tin (IV) chloride [4.9 mL (10.91 g) 41.9 mmoles] was added to the toluene/diethyl ether solution and the resultant slurry was immediately cooled to and held at 0° C. with an acetone/dry ice bath. 1-Hexene [3.1 mL (2.10 g) 25.0 mmoles] and nitromethane [3.3 mL (3.72 g) 60.9 mmoles] were added to the sulfinyl chloride solution and the resultant solution was cooled to 0° C. with an acetone/dry ice bath. The 0° C. tin (IV) chloride/diethyl ether/toluene slurry was added to the 0° C. sulfinyl chloride in 5 to 10 seconds using 5 mL of toluene rinse. The resultant slurry was allowed to exotherm to 21° to 23° C. and stir for four hours under nitrogen.

The slurry was filtered, washed with 25 mL of toluene and returned to the reaction flask with 80 mL of methyl alcohol. The resultant slurry was stirred and allowed to crystallize at 21° to 23° C. for 15 minutes. The slurry was then cooled to 0° to 5° C. and stirred for another three hours and forty-five minutes. No water was added during the methyl alcohol stir.

The slurry was filtered and the product was washed with 30 mL of methyl alcohol. The light colored solid was dried in a vacuum oven at 45° to 60° C. for 15 to 16 hours. The assay corrected isolated yield of (1) was 72.2% (9.16 g, theoretical=12.34 g) and the purity was determined to be 97.3% by replicate HPLC assay.

EXAMPLE 10

Example 5 (above) was repeated except: diethyl ether [2.5 mL (1.76 g) 23.9 mmoles] was utilized as described in Example 1, and nitrobenzene [6.6 mL (8.21 g) 64.1 mmoles] was used in place of nitromethane. The sulfinyl chloride/tin (IV) chloride/diethyl ether/toluene/ nitrobenzene slurry was also only allowed to stir for 90 minutes at 21° to 23° C. rather than four hours. The assay corrected isolated yield of (1) was 70.5% (9.50 g, theoretical=12.74 g) and the purity was determined to be 94.6% by replicate HPLC assay.

EXAMPLE 11

Example 5 (above) was repeated except: diethyl ether [2.5 mL (1.76 g) 23.9 mmoles] was utilized as described in Example 1, and 1-nitropropane [5.7 mL (5.68 g) 63.8 mmoles was used in place of nitromethane. The sulfinyl chloride/tin (IV) chloride/diethyl ether/toluene/ 1-nitropropane slurry was also only allowed to stir for 90 minutes at 21° to 23° C. rather than four hours. The assay corrected isolated yield of (1) was 69.7% (9.13 g, theoretical=12.74 g) and the purity was determined to be 97.2% by replicate HPLC assay.

EXAMPLE 12

Example 5 (above) was repeated except: diethyl ether [2.5 mL (1.76 g) 23.9 mmoles] was utilized as described in Example 1, and nitroethane [4.6 mL (4.80 g) 64.0 mmoles] was used in place of nitromethane. The sulfinyl chloride/tin (IV) chloride/diethyl ether/toluene/ nitroethane slurry was also only allowed to stir for 90 minutes at 21° to 23° C. rather than four hours. The assay corrected isolated yield of (1) was 69.5% (9.18 g, theoretical=12.74 g) and the purity was determined to be 96.4% by replicate HPLC assay.

EXAMPLE 13

A 500 mL three-necked round bottomed flask was equipped with a mechanical stirrer, a nitrogen inlet, and a thermometer. The reaction flask was charged with 220 mL of a toluene solution of sulfinyl chloride (25.5 mmoles based on (1B)-6-[(phenoxyacetyl)amino]-penicillanic acid, (4-nitrophenyl) methyl ester-1-oxide. This sulfinyl chloride solution was cooled to 15° C. before titanium (IV) chloride [5.6 mL (9.69 g) 51.1 mmoles] was added neat via a volumetric pipette. The resultant slurry was immediately warmed to and held at 60° C. under a nitrogen environment for a total reaction time of four hours.

The slurry was filtered, washed with 25 mL of toluene and returned to the reaction flask with 70 mL of methyl alcohol. The resultant slurry was stirred and allowed to crystallize at 21° to 23° C. for 15 minutes. The slurry was then cooled to 0° to 5° C. and stirred for another three hours and forty-five minutes. No water was added during the methyl alcohol stir.

The slurry was filtered and the product was washed with 30 mL of methyl alcohol. The light colored solid was dried in a vacuum oven at 45° to 60° C. for 15 to 16 hours. The assay corrected isolated yield of (1) was 65.4% (8.82 g, theoretical=12.74 g) and the purity was determined to be 94.4% by replicate HPLC assay.

EXAMPLE 14

Example 13 (above) was repeated except: nitromethane [2.8 mL (3.16 g) 51.7 mmoles] was added to the toluene solution of sulfinyl chloride before it was cooled to 15° C. and the titanium (IV) chloride was added. The assay corrected isolated yield of (1) was 68.8% (9.45 g, theoretical=12.74 g) and the purity was determined to be 92.7% by replicate HPLC assay.

EXAMPLE 15

Example 13 (above) was repeated except: nitromethane [3.5 mL (3.94 g) 64.6 mmoles] and 1-hexene [3.2 mL (2.17 g) 25.8 mmoles] was added to the toluene solution of sulfinyl chloride before it was cooled to 15° C. and the titanium (IV) chloride was added. The sulfinyl chloride/titanium (IV) chloride/nitromethane/ 1-hexene slurry was also only allowed to stir for three hours at 60° C. rather than four hours. The assay corrected isolated yield of (1) was 68.2% (8.99 g, theoretical = 12.74 g) and the purity was determined to be 96.7% by replicate HPLC assay.

EXAMPLE 16

A 500 mL three-necked round bottomed flask was equipped with a mechanical stirrer, a nitrogen inlet, and a thermometer. The reaction flask was charged with 216 mL of a toluene solution of sulfinyl chloride (25.5 mmoles based on (1B)-6-[(phenoxyacetyl)amino]-penicillanic acid, (4-nitrophenyl) methyl ester-1-oxide. This sulfinyl chloride solution was cooled to 5° C. Zirconium (IV) chloride [20.3 g (99.6% purity) 86.8 mmoles] was weighed into a 50 ml round bottomed flask in a nitrogen filled glove bag. The 50 mL flask was capped and 25 mL of toluene was added via a syringe. The zirconium (IV) chloride/toluene slurry was added to the 5° C. toluene solution of sulfinyl chloride using an additional 25 mL of toluene as a rinse. The resultant slurry was allowed to exotherm to 21°-23° C. and stir for 48 hours under nitrogen. HPLC analysis indicated that the reaction had not progressed to completion so the slurry was heated to and held at 60° C. for three hours.

The slurry was filtered and returned to the reaction flask with 70 mL of methyl alcohol. No product crystallized out from the methyl alcohol treatment, so (1) was not recovered.

EXAMPLE 17

A 500 mL three-necked round bottomed flask was equipped with a mechanical stirrer, a nitrogen inlet, and a thermometer. The reaction flask was charged with 136 mL of a toluene solution of sulfinyl chloride (19.3 mmoles based on (1B)-6-[(phenoxyacetyl)amino]-penicillanic acid, (4-nitrophenyl) methyl ester-1-oxide. This sulfinyl chloride solution was cooled to 15° C. Zirconium (IV) chloride [7.7 g (99.6% purity) 32.9 mmoles] was weighed into a 50 ml round bottomed flask in a nitrogen filled glove bag. The 50 mL flask was capped and 25 mL of toluene and diethyl ether [1.9 mL (1.34 g) 18.1 mmoles) was added via a syringe. The zirconium (IV) chloride/diethyl ether/toluene slurry was cooled to 0° C. with an acetone/dry ice bath before it was added to the 15° C. toluene solution of sulfinyl chloride. Toluene (5 mL) was used to rinse in the reagents. The resultant slurry was allowed to exotherm to 21° to 23° C. and stir for 18 hours under nitrogen. HPLC analysis indicated that the reaction had not progressed to completion so the slurry was heated to and held at 60° C. for one hour.

The slurry was filtered and returned to the reaction flask with 55 mL of methyl alcohol. The resultant slurry was stirred and allowed to crystallize at 21° to 23° C. for 15 minutes. Deionized water (10 mL) was added to the slurry and the resultant slurry was then cooled to 0°-5° C. and stirred for another hour.

The slurry was filtered and the product was washed with 20 mL of methyl alcohol. The light colored solid was dried in a vacuum oven at 45° to 60° C. for 15 to 16 hours. The assay corrected isolated yield of (1) was 32.1% (3.36 g, theoretical = 9.64 g) and the purity was determined to be 92.0% by replicate HPLC assay.

EXAMPLE 18

A 500 mL three-necked round bottomed flask was equipped with a mechanical stirrer, a nitrogen inlet, and a thermometer. The reaction flask was charged with 216 mL of a toluene solution of sulfinyl chloride (25.5 mmoles based on (1B)-6-[(phenoxyacetyl)amino]-penicillanic acid, (4-nitrophenyl) methyl ester-1-oxide. Nitromethane [80 mL (90.16 g) 1.48 moles] was added to the sulfinyl chloride solution and the resultant solution was cooled to 15° C. Zirconium (IV) chloride [10.1 g (99.6% purity) 43.2 mmoles] was weighed into a 50 ml round bottomed flask in a nitrogen filled glove bag. The 50 mL flask was capped and toluene (25 mL) was added via a syringe. The zirconium (IV) chloride/toluene slurry was cooled to 0° C. with an acetone/dry ice bath before it was added to the 15° C. toluene solution of sulfinyl chloride/nitromethane. A solution developed initially, but a solid began to precipitate after six minutes. The reaction was allowed to exotherm to 21° to 23° C. and stir for 105 minutes. More nitromethane [35 mL (39.45 g) 646.2 mmoles] was added during this reaction time to keep the reaction mixture homogeneous. The reaction solution was transferred to a round bottomed flask (for vacuum evaporation) using additional nitromethane [35 mL (39.45 g) 646.2 mmoles] to aid with the transfer.

The reaction solution was evaporated under vacuum to an oil and 70 mL of methyl alcohol was added. The resultant slurry was cooled and stirred at 0° to 5° C. for 100 minutes. Deionized water (15 mL) was added 50 minutes into the methyl alcohol treatment.

The slurry was filtered and the product was washed with 30 mL of methyl alcohol. The light colored solid was dried in a vacuum oven at 45° to 60° C. for 15 to 16 hours. The assay corrected isolated yield of (1) was 66.2% (8.76 g, theoretical = 12.74 g) and the purity was determined to be 96.4% by replicate HPLC assay.

TABLE 1A

| | | Lewis Acid = Tin (IV) Chloride (1.7 eq.) | | | | |
|---|---|---|---|---|---|---|
| Exp. | Complex Formation Temperature | Reaction Time (Temperature) | Ethyl ether | Nitro Compound | 1-Hexene | Corrected Isolated Yield |
| 1 | 15° C. | 18 hrs (21-23° C.) | .93 eq | none | none | 68.10% |
| 2 | −50° C. | 18 hrs (21-23° C.) | .93 eq | none | none | 65.30% |
| 3 | −10° C. | 18 hrs (21-23° C.) | .93 eq | none | none | 66.30% |
| 4 | 15° C. | 18 hrs (21-23° C.) | none | none | none | 50.50% |
| 5 | −10° C. | 4 hrs (21-23° C.) | none | nitromethane (2.5 eq) | none | 60.90% |
| 6 | −10° C. | 4 hrs (21-23° C.) | none | nitromethane (2.5 eq) | 1 eq | 65.20% |
| 7 | 10° C. | 4 hrs | .93 eq | none | 1 eq | 70.00% |

TABLE 1A-continued

| | | Lewis Acid = Tin (IV) Chloride (1.7 eq.) | | | | |
|---|---|---|---|---|---|---|
| Exp. | Complex Formation Temperature | Reaction Time (Temperature) | Ethyl ether | Nitro Compound | 1-Hexene | Corrected Isolated Yield |
| 8 | −8° C. | 90 min (21-23° C.) | .93 eq | nitromethane (2.5 eq) | none | 71.10% |
| 9 | 0° C. | 2 hrs (21-23° C.) | .93 eq | nitromethane (2.5 eq) | 1 eq | 72.20% |
| 10 | −8° C. | 90 min (21-23° C.) | .93 eq | nitrobenzene (2.5 eq) | none | 70.50% |
| 11 | −10° C. | 90 min (21-23° C.) | .93 eq | 1-nitropropane (2.5 eq) | none | 69.70% |
| 12 | −10° C. | 90 min (21-23° C.) | .93 eq | nitroethane (2.5 eq) | none | 69.50% |

TABLE 1B

| | | Lewis Acid = Titanium (IV) Chloride (2.0 eq.) | | | | |
|---|---|---|---|---|---|---|
| Exp. | Complex Formation Temperature | Reaction Time (Temperature) | Ethyl ether | Nitro Compound | 1-Hexene | Corrected Isolated Yield |
| 13 | 15° C. | 4 hrs (60° C.) | none | none | none | 65.40% |
| 14 | 15° C. | 4 hrs (60° C.) | none | nitromethane (2.0 eq) | none | 68.80% |
| 15 | 15° C. | 3 hrs (60° C.) | none | nitromethane (2.5 eq) | 1 eq | 68.20% |

TABLE 1C

| | | (Lewis Acid = Zirconium (IV) Chloride (3.4 eq and 1.7 eq)) | | | | |
|---|---|---|---|---|---|---|
| Exp. | Complex Formation Temperature | Reaction Time (Temperature) | Ethyl ether | Nitro Compound | 1-Hexene | Corrected Isolated Yield |
| 16 | 5° C. | 48 hrs (21-23° C.) + 3 hrs (60° C.) | none | none | none | 0 |
| 17 | 15° C. | 18 hrs (21-23° C.) + 1 hrs (60° C.) | .93 eq | none | none | 32.10% |
| 18 | 15° C. | 105 min (21-23° C.) | none | nitromethane (21.2 moles, 83.3 eq) | none | 66.20% |

Turning now to the FIG. 1, illustrated are isothermal reactions of nitromethane modified tin (IV) chloride assisted ring closures. The following define the symbols used in the figures:

— 15° C., nitromethane (A1)
— 15° C. (A2)
— 0° C., nitromethane (B1)
—0° C. (B2)
— −15° C., nitromethane (C1)
□— −15° C. (C2)

The runs were performed according to Experiment 1, with and without the addition of nitromethane (2.5 equivalents) at the stated temperatures of the sulfinyl chloride. FIG. 1 indicates that reactions in the presence of the nitromethane exhibited faster ring closure rates as compared to those without nitromethane. Further, the yield of exomethylene with nitromethane is higher than without.

Figure 2:
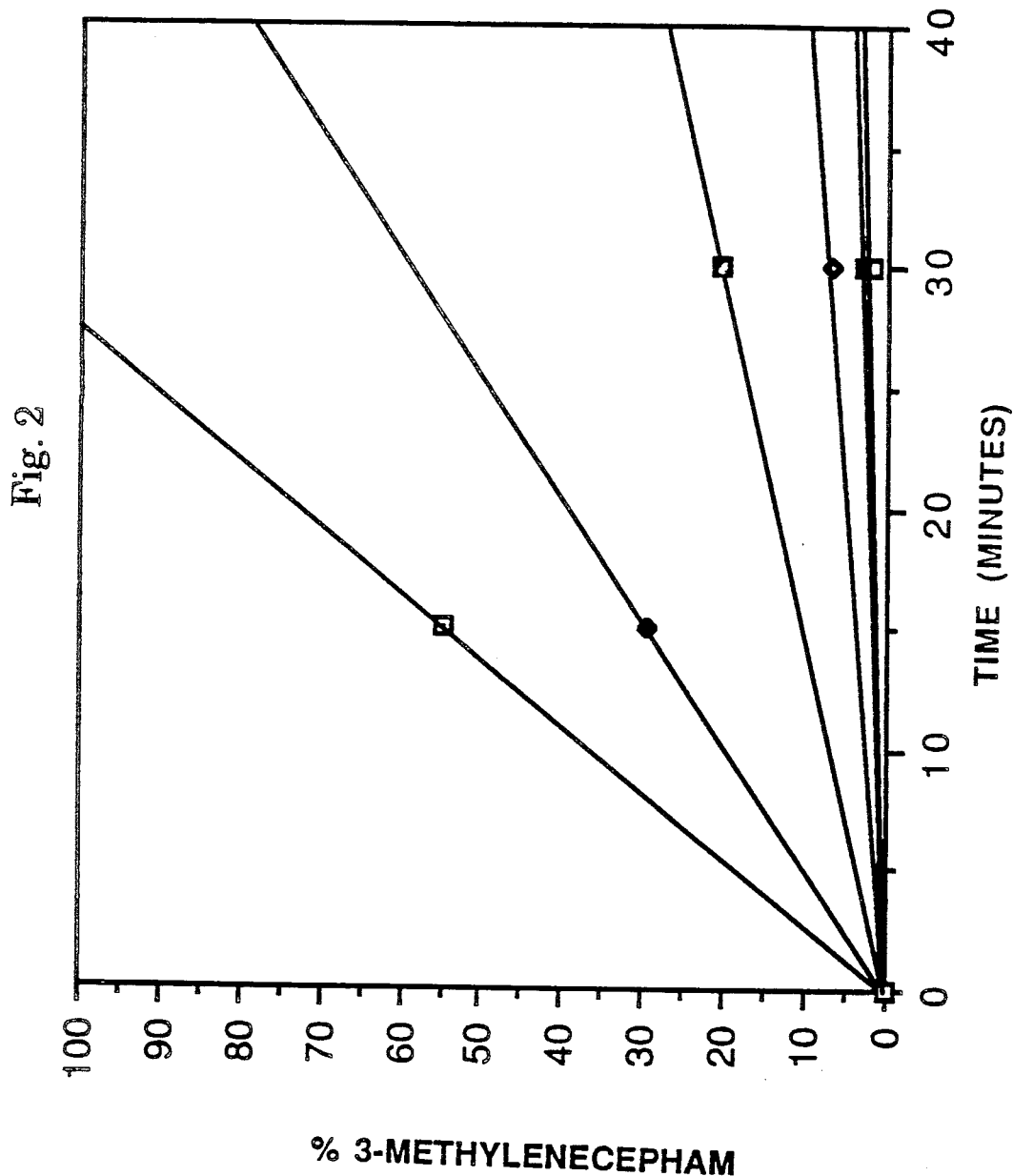
FIG. 2 is a graph illustrating magnitude of rate comparisons of the reaction rates for FIG. 1.

FIG. 2 is a mathematical representation of rate comparisons, and illustrates that during the first 30 minutes of reaction, the rate of ring closure (% exomethylene formation) is enhanced by 85%, 191% and 41% at 15° C., 0° C., and −15° C. respectively Mathematically, A1 is represented by the equation Y=3.6467X, and A2 is represented by Y=1.9667X. B1 is mathematically represented by Y=0.68000X while B2 is represented by Y=0.23333X. C1 is represented by Y=0.10333X and C2, Y=7.3333X10$^{-2}$.

We claim:

1. A process for preparing a 3-exomethylenecepham sulfoxide ester of the formula

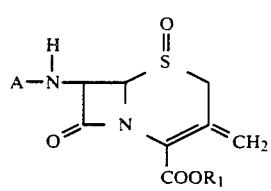

(1)

wherein A is an amino protecting group or a group of the formula

wherein R is the residue of a carboxylic acid and $R_1$ is a carboxylic acid protecting group, which comprises combining chlorosulfinylazetidinone of the formula

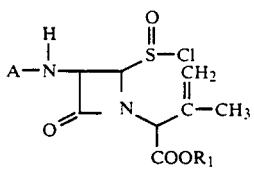   (2)

in an inert solvent under substantially anhydrous conditions with a Lewis acid-type Friedel-Crafts catalyst, and a nitro compound, said nitro compound selected from $C_1$-$C_6$ nitroalkanes, nitrotoluene and nitrobenzene, at a temperature and time sufficient to provide the compound of formula (1).

2. The process as recited in claim 1 wherein said nitro compound is selected from the group consisting of nitromethane, nitroethane, nitrobenzene, or nitropropane.

3. The process as recited in claim 1 wherein said Lewis acid-type Friedel-Crafts catalyst is selected from a group consisting of titanium chloride, zirconium chloride, or stannic chloride.

4. The process as recited in claim 1 wherein the step of combining is performed in the presence of an unsaturated compound.

5. The process of claim 4 wherein the unsaturated compound is a non-conjugated $C_5$-$C_{10}$ alkadiene.

6. The process of claim 4 wherein the unsaturated compound is a $C_3$-$C_{10}$ allene.

7. The process of claim 4 wherein the unsaturated compound is a $C_5$-$C_{10}$ cycloalkene.

8. The process of claim 7 wherein the cycloalkene is cyclopentene or cyclohexene.

9. The process of claim 4 wherein the unsaturated compound is a $C_2$-$C_{10}$ alkene.

10. The process of claim 9 wherein the alkene is a $C_5$-$C_8$ alkene.

11. The process of claim 10 wherein the alkene is a straight chain or branched chain alkene.

12. The process of claim 11 wherein the alkene is 1-pentene, 1-hexene, 2-hexene, 1-heptene or 1-octene.

13. The process as recited in claim 1 wherein the step of combining is performed in the presence of an oxo compound.

14. The process of claim 13 wherein the oxo compound is of the formulae $R_2$—O—$R_2$, Z

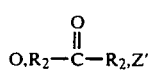

C=O or $(R'_2)_3$—P→O,
wherein each $R_2$ is independently $C_1$-$C_4$ alkyl; each $R'_2$ is independently $C_1$-$C_4$ alkyl, $C_5$-$C_6$ cycloalkyl, phenyl or phenyl substituted by $C_1$-$C_4$ alkyl, $C_1$-$C_4$ alkoxy or halogen; Z is $+CH_2\}_m$, —$CH_2CH_2$—O—$CH_2CH_2$—, or —$CH_2$—O$(CH_2)_3$; m is 4 or 5; and Z' is

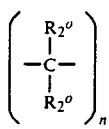

wherein each $R^o{}_2$ is hydrogen or $C_1$-$C_4$ alkyl, and n is 3 to 6.

15. The process of claim 14 wherein A is of the formula

and R is benzyl, phenoxymethyl or 2-thienyl and $R_1$ is benzyl or substituted benzyl.

16. The process of claim 15 wherein R is phenoxymethyl and $R_1$ is p-nitrobenzyl.

17. The process of claim 16 wherein the oxo compound is of the formula $R_2$—O—$R_2$ or

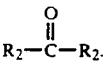

18. The process of claim 17 wherein the oxo compound is diethyl ether or acetone.

19. The process of claim 1 wherein the step of combining is performed in the presence of an oxo compound and an unsaturated compound.

20. The process of claim 19 wherein the unsaturated compound is present in an amount corresponding to between about 1 mole to about 2 moles, and the oxo compound is present in an amount corresponding to between about 0.75 moles to about 2 moles, per mole of 4-chlorosulfinylazetidinone.

21. The process of claim 20 wherein A is a group of the formula

and R is phenoxymethyl, $R_1$ is 4-nitrobenzyl, the oxo compound is diethyl ether, and the unsaturated compound is a $C_5$-$C_8$ alkene.

22. The process of claim 21 wherein the alkene is a straight chain alkene.

23. The process as recited in claim 1 wherein the temperature is between about $-15°$ C. and about $60°$ C.

24. The process as recited in claim 23 wherein said temperature is between about $-10°$ C. to about $0°$ C.

25. A process for preparing a 3-oxo-methylenesulfoxide ester of the formula

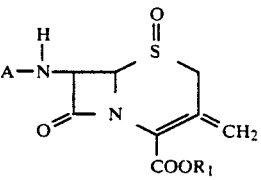   (1)

wherein A is an amino protecting group or a group of the formula

wherein R is a residue of a carboxylic acid and $R^1$ is a carboxylic acid protecting group, which comprises combining chlorosulfinylazedininone of the formula

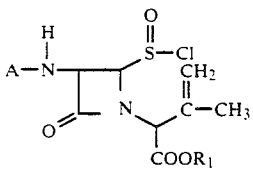 (2)

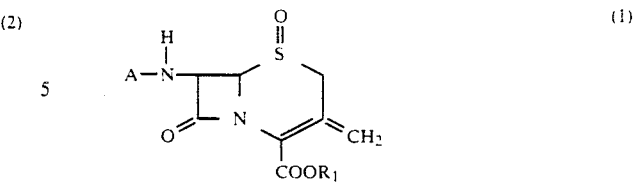 (1)

wherein A is an amino protecting group or a group of the formula $$R-\overset{O}{\underset{\|}{C}}-$$

wherein R is the residue of a carboxylic acid and $R_1$ is a carboxylic acid protecting group, which comprises combining chlorosulfinylazetidinone of the formula

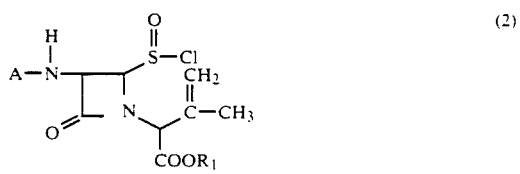 (2)

in an inert solvent under substantially anhydrous conditions with between about 1.0 and about 3 moles per mole of the azetidinone of a Lewis acid-type Friedel-Crafts catalyst selected from the group consisting of titanium chloride, zirconium chloride, and stannic chloride, between about 0.75 and about 2 moles per mole of the azetidinone of an oxo compound, between about 1 and about 2 moles per mole of the azetidinone of an unsaturated compound and about 1 to 4 moles per mole of the azetidinone of a nitro compound selected from the group consisting of nitromethane, nitroethane, nitrobenzene, and nitropropane at a temperature of between about −15° C. to 60° C. for a time sufficient to provide the compound of formula (1).

34. The process as recited in claim 33 wherein said unsaturated compound is 1-hexene.

35. The process as recited in claim 33 wherein said oxo compound is diethyl ether or acetone.

36. The process as recited in claim 33 wherein said temperature is between about −10° C. and about 0° C.

37. The process as recited in claim 33 wherein said Lewis acid-type catalyst is stannic chloride.

38. The process as recited in claim 37 wherein said nitro compound is nitromethane in the amount of about 2.5 mole per mole of the azetidinone.

39. The process as recited in claim 33 wherein A is a group of the formula $$R-\overset{O}{\underset{\|}{C}}-$$

and R is benzyl, phenoxymethyl, or 2-thienyl and $R^1$ is benzyl or substituted benzyl.

* * * * * in an inert solvent under substantially anhydrous conditions with a Lewis acid-type Friedel-Crafts catalyst selected from a group consisting of titanium chloride, zirconium chloride, and stannic chloride, a nitro compound selected from the group consisting of nitromethane, nitroethane, nitrobenzene, and nitropropane, at a temperature of between about −15° C. to about 60° C. for a time sufficient to provide the compound of formula (1).

26. The process as recited in claim 25 wherein said step of combining is performed in the presence of an unsaturated compound selected from the group of $C_2$–$C_{10}$ olefin, a $C_3$–$C_{10}$ cyclolefin, a $C_6$–$C_{10}$ non-conjugated diolefin, a $C_3$–$C_{10}$ allene, and a $C_6$–$C_{10}$ non-conjugated cyclodiene.

27. The process as recited in claim 25 wherein said step of combining is performed in the presence of an oxo compound.

28. The process as recited in claim 25 wherein said step of combining is performed in the presence of an unsaturated compound and an oxo compound.

29. The process as recited in claim 28 wherein said nitro compound is nitromethane and said Lewis acid-type Friedel-Crafts catalyst is stannic chloride.

30. The process as recited in claim 29 wherein said nitromethane is present in an amount between about 1 to about 4 moles per mole of the azetidinone, the Friedel-Crafts catalyst is present in an amount between about 1.0 and 3 moles per mole of the azetidinone, the oxo compound is present in the amount of about 0.75 and about 2 moles per mole of the azetidinone, and said unsaturated compound is present in an amount between about 1 and about 2 moles per mole of the azetidinone.

31. The process as recited in claim 30 wherein said unsaturated compound is 1-hexene and said oxo compound is diethyl ether.

32. The process as recited in claim 31 wherein A is a group of the formula $$R-\overset{O}{\underset{\|}{C}}-$$

and R is benzyl, phenoxymethyl, or 2-thienyl, and $R^1$ is benzyl or substituted benzyl.

33. A process for preparing a 3-exomethylenecepham sulfoxide ester of the formula

UNITED STATES PATENT AND TRADEMARK OFFICE
CERTIFICATE OF CORRECTION

PATENT NO.    :    5,126,446                          Page 1 of 3

DATED         :    June 30, 1992

INVENTOR(S)   :    Frank Brown, Jr., Francis O. Ginah, and
                   Leonard L. Winneroski It is certified that an error appears in the above-identified patent and that said Letters Patent is hereby corrected as shown below:

Column 2, delete the first structural formula and insert therefor

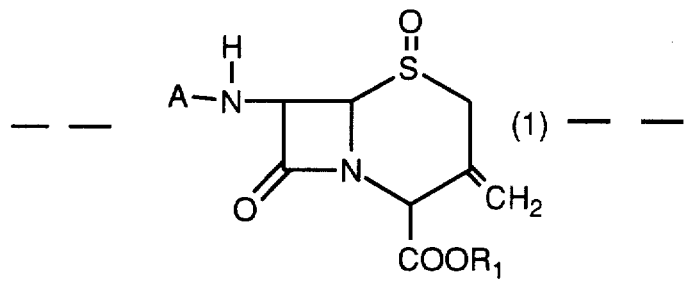

Column 4, delete the last structural formula and insert therefor

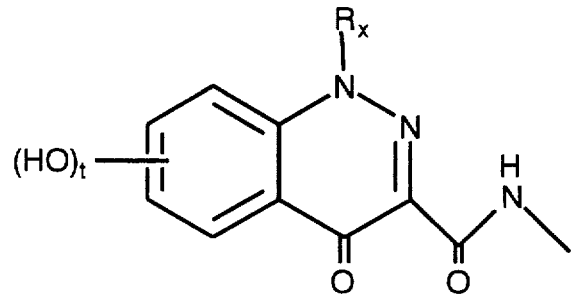

UNITED STATES PATENT AND TRADEMARK OFFICE
CERTIFICATE OF CORRECTION

PATENT NO. : 5,126,446            Page 2 of 3

DATED : June 30, 1992

INVENTORS : Frank Brown, Jr., Francis O. Ginah, and Leonard L. Winneroski

It is certified that an error appears in the above-identified patent and that said Letters Patent is hereby corrected as shown below:

Column 22, delete the first structural formula and insert therefor:

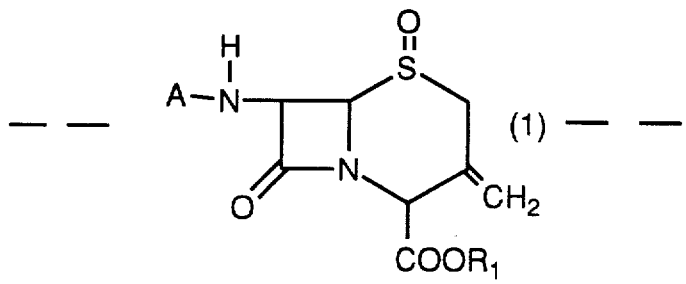

Column 24, lines 50-58, delete the structural formula therein and insert therefor:

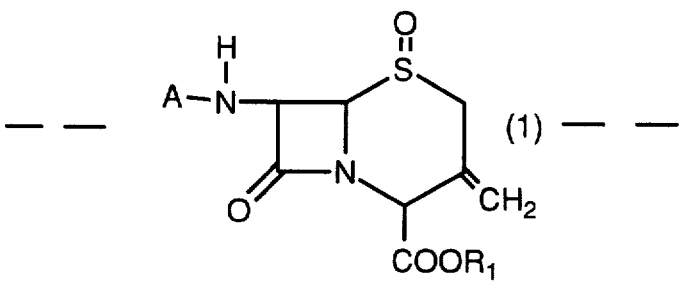

UNITED STATES PATENT AND TRADEMARK OFFICE
CERTIFICATE OF CORRECTION

PATENT NO. : 5,126,446
DATED : June 30, 1992
INVENTOR(S) : Frank Brown, Jr., Francis O. Ginah, and Leonard L. Winneroski It is certified that error appears in the above-indentified patent and that said Letters Patent is hereby corrected as shown below:

Col. 25, line 23, delete "$C_3$" and insert therefor --$C_5$--

Col. 25, line 23, delete "$C_6$" and insert therefor --$C_5$--

Signed and Sealed this

Eighteenth Day of January, 1994

Attest:

BRUCE LEHMAN

Attesting Officer

Commissioner of Patents and Trademarks